United States Patent
Zucchi et al.

(10) Patent No.: US 8,091,548 B2
(45) Date of Patent: Jan. 10, 2012

(54) ANTI-CONDENSATION DEVICE FOR CATHETERS

(75) Inventors: Giuseppe Zucchi, San Possidonio (IT); Daniele Resca, S. Felice sul Panaro (IT); Samuele Pizzo, Revere (IT)

(73) Assignee: Covidien AG, Neuhausen am Rheinfall (CH)

( * ) Notice: Subject to any disclaimer, the term of this patent is extended or adjusted under 35 U.S.C. 154(b) by 591 days.

(21) Appl. No.: 12/270,114

(22) Filed: Nov. 13, 2008

(65) Prior Publication Data
US 2009/0165792 A1    Jul. 2, 2009

(30) Foreign Application Priority Data

Dec. 28, 2007  (EP) ..................... 07425836

(51) Int. Cl.
*F24J 3/00* (2006.01)
(52) U.S. Cl. .......... 128/204.17; 128/203.16; 128/203.17
(58) Field of Classification Search ............. 128/201.13, 128/203.16, 203.17, 204.17, 204.22
See application file for complete search history.

(56) References Cited

U.S. PATENT DOCUMENTS

| | | | |
|---|---|---|---|
| 3,616,796 A | 11/1971 | Jackson |
| 5,031,612 A | 7/1991 | Clementi |
| 5,988,164 A | 11/1999 | Paluch |

FOREIGN PATENT DOCUMENTS

| | | |
|---|---|---|
| EP | 0579384 | 1/1994 |
| EP | 1262209 | 12/2002 |
| WO | 03022342 | 3/2003 |

OTHER PUBLICATIONS

European Search Report, dated Apr. 25, 2008.

*Primary Examiner* — Glenn Richman
(74) *Attorney, Agent, or Firm* — Carter, DeLuca, Farrell & Schmidt LLP

(57) ABSTRACT

An anti-condensation arrangement for catheters including a heated air generator, a sheath covering a catheter such as to create a cavity with it, and a device for the input of heated air produced by the generator into the cavity wherein the sheath has a venting opening to allow the exit of heated air from the cavity and therefore continuous exchange of air.

9 Claims, 1 Drawing Sheet

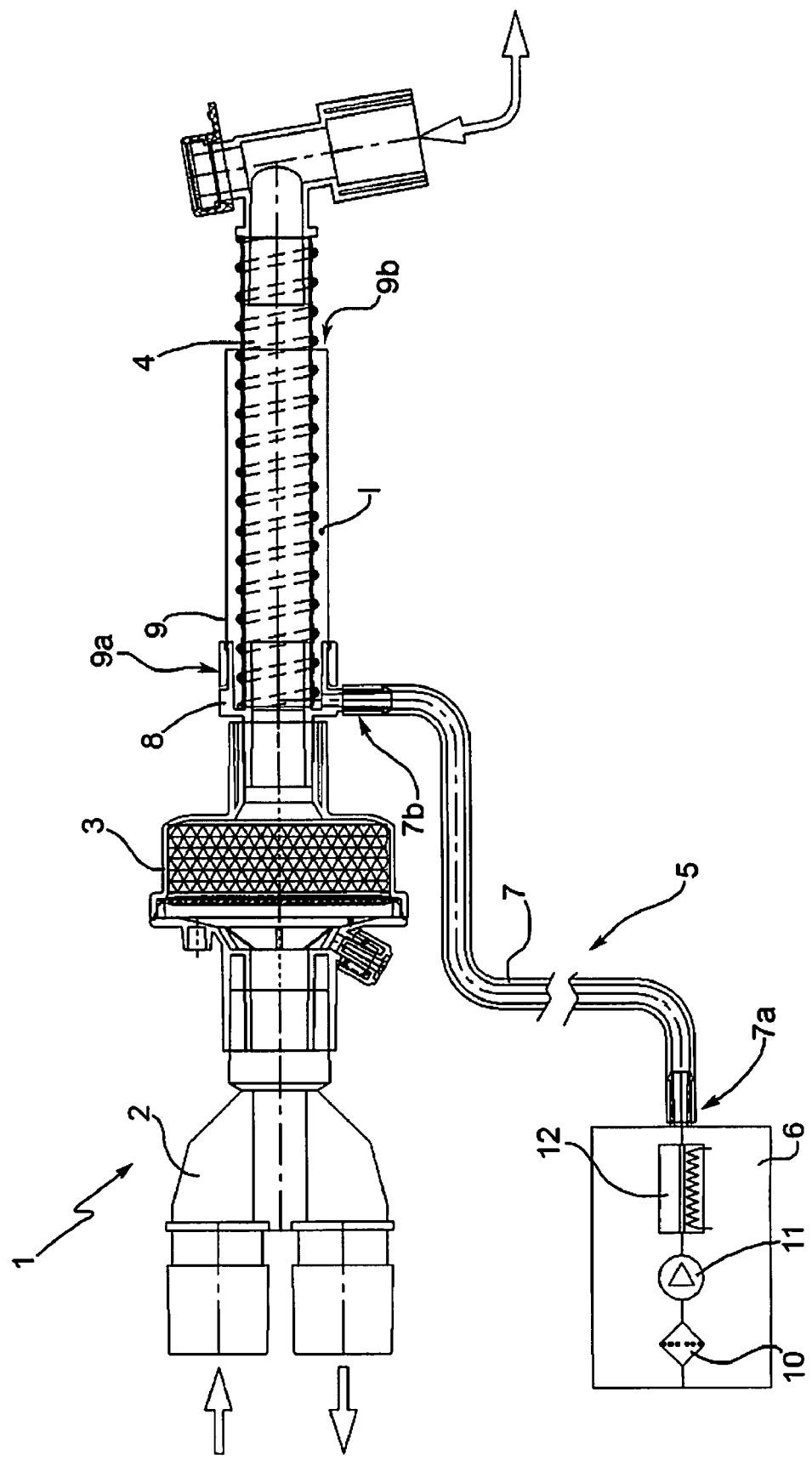

ANTI-CONDENSATION DEVICE FOR CATHETERS

The present invention relates to an anti-condensation device for catheters. In particular the teachings of the present invention may be applied in a particularly advantageous way to the so-called "catheter mounts".

As is known, catheter mounts are used in combination with breathing circuits and their purpose is to interface the breathing circuit with the tracheal or tracheostomy tube of the patient under mechanical ventilation. Generally, catheter mounts are used in anesthesia and intensive care units (ICU), but also in Home Care.

Inside the catheter mount, therefore, there is always a passage of air from and to the patient, with the consequent presence of condensation due to the water vapour contained in the respiratory flow.

The presence of condensation in catheter mounts leads to a series of problems due mainly to the possibility that the water that forms may obstruct the tracheal tube, with the result of increasing resistances to the respiratory flow, or it may flow towards the lungs, with the risk of a drastic decrease of pulmonary functions. Moreover, the condensation that forms in the catheter mount may be a vehicle for the bacteria present inside the circuit. For these reasons, in the presence of condensation the nursing staff must carry out a pulmonary hygiene operation (broncho-aspiration), which may be particularly irritating for the patient. These problems are mainly felt in ICUs, where the patient remains under mechanical ventilation for several days.

To avoid the formation of condensation, various solutions are known which make use of electrical heating of the catheter mount. As may seem obvious, although these solutions are able to guarantee the absence of condensation, nevertheless the presence of an electric current near the patient and, what's more, in an environment where there are several medical appliances, may cause problems.

The aim of the present invention is to provide an anti-condensation device for catheter mounts with technical characteristics such as to overcome the inconveniences of the prior art.

The object of the present invention is an anti-condensation arrangement for catheters characterised in that it comprises a heated air generator, a sheath surrounding at least a part of a catheter such as to create a cavity between said sheath and said part of the catheter, and a device for inputting heated air produced by said generator into said cavity; said sheath having a venting opening to allow the exit of heated air from said cavity.

The following example is given for illustrative purposes without limitation, for a better understanding of the invention with the aid of the accompanying drawing, which is a schematic view of the anti-condensation device to which the present invention refers, fitted on a catheter mount.

In the FIGURE, reference 1 indicates a ventilation apparatus comprising a Y-shaped connector 2 set to convey both the inspired flow and the expired flow under the effect of a mechanical ventilator V (schematically illustrated), a filtering device 3 connected to the Y-shaped connector 2 and composed of the coupling of a filter and of a HME (Heat and Moisture Exchanger), and a corrugated catheter mount 4 connected between the filtering device 3 and a patient P 14 (schematically illustrated) through a patient mouth piece (not shown). In the FIGURE, reference 5 indicates an anti-condensation device as a whole, according to the present invention. The anti-condensation device 5 comprises a heated air generator 6, a connecting hose 7, a radial diffuser 8 and a sheath 9.

The heated air generator 6 comprises, in turn, a filter 10, a pump 11 and a heater 12. The connecting hose 7 presents a first end 7a connected to the heated air generator 6 and a second end 7b connected to the radial diffuser 8, which is housed at one end of the catheter mount 4 and has the function of both ensuring a uniform diffusion of heated air around the catheter mount 4 and connecting the catheter mount 4 itself to the filtering device 3.

The sheath 9 has a tubular shape and surrounds at least a part of the catheter mount 4, in such a way as to create with it a cavity I in relation to said catheter mount. Thus, at least a part of the catheter mount is located inside the tubular sheath, wherein the space defined by the distance between the catheter mount, located inside the sheath, and the sheath itself constitutes the cavity I, into which the heated air flows. It should be appreciated in another embodiment that the sheath also could surround and cover the full length of the catheter mount. In yet another embodiment, it should be realized that the sheath could be used for any type of catheter in order to prevent formation of condensation inside the catheter. In particular, the sheath 9, at its first end 9a, is fitted in a fluid-tight way to the radial diffuser 8, and it has a second end 9b open so as to ensure in the cavity I a continuous flow of heated air sent in by the radial diffuser 8. Moreover, the sheath 9 is made of flexible and transparent material to inspect visually the inside of the catheter mount 4 and thus check that there is no formation of condensation.

In use, the heated air is produced by the generator 6 and it is conveyed through the connecting hose 7 to the radial diffuser 8, through which it is sent into the cavity I to come out at the open end 9b of the sheath 9. The passage of heated air into the cavity I causes heating of the catheter mount 4, thus avoiding the formation of condensation.

As explained in the above description, the anti-condensation device of the present invention simply guarantees avoiding the formation of condensate in the catheter, without using any electrical components in direct contact with the catheter itself, but exploiting a suitable conveyed flow of heated air.

We claim:

1. Anti-condensation arrangement for catheters, comprising:
   a heated air generator,
   a sheath surrounding at least a part of a catheter such as to create a cavity between said sheath and said part of the catheter, and
   a device for inputting heated air produced by said generator into said cavity; said sheath having a venting opening to allow the exit of heated air from said cavity;
   a radial diffuser arranged around an outer surface of the catheter and to which the sheath is fitted in a fluid-tight way.

2. Anti-condensation arrangement according to claim 1, said device comprising:
   a connecting hose connected to said heated air generator and the radial diffuser.

3. Anti-condensation arrangement according to claim 1, wherein the sheath is fixed at a first end to the radial diffuser and presents a second open end.

4. Anti-condensation arrangement according to claim 3, wherein the sheath is made of flexible transparent material.

5. Anti-condensation arrangement according to claim 1, said heated air generator comprising:
- a filter,
- a pump, and
- a heater.

6. Anti-condensation arrangement according to claim 1, wherein said catheter is a catheter mount.

7. Anti-condensation arrangement according to claim 6, wherein said catheter mount is connected to a filtering device.

8. Anti-condensation arrangement according to claim 1, comprising a device to supply heated air around the outer surface of said catheter.

9. Ventilation apparatus for use in an intensive care unit, comprising an anti-condensation arrangement according to claim 1.

* * * * *